(12) United States Patent
Duremdes et al.

(10) Patent No.: US 9,795,298 B2
(45) Date of Patent: Oct. 24, 2017

(54) SYSTEM AND METHOD FOR TRANSMITTING, RECEIVING AND ANALYSING PARTOGRAPH INFORMATION

(71) Applicant: SMART HUB PTE. LTD., Singapore (SG)

(72) Inventors: Ramon G. Duremdes, Makati (PH); Ian Christopher De Jesus, Makati (PH); Kristian R. Sumabat, Makati (PH); Kathryn T. Genson, Makati (PH)

(73) Assignee: EINNOVATIONS HOLDINGS PTE. LTD., Singapore (SG)

( * ) Notice: Subject to any disclaimer, the term of this patent is extended or adjusted under 35 U.S.C. 154(b) by 174 days.

(21) Appl. No.: 14/365,598

(22) PCT Filed: Dec. 13, 2012

(86) PCT No.: PCT/SG2012/000473
§ 371 (c)(1),
(2) Date: Jun. 13, 2014

(87) PCT Pub. No.: WO2013/089645
PCT Pub. Date: Jun. 20, 2013

(65) Prior Publication Data
US 2014/0323922 A1 Oct. 30, 2014

(30) Foreign Application Priority Data
Dec. 13, 2011 (SG) .................. 201109211

(51) Int. Cl.
*A61B 5/00* (2006.01)
*G06F 19/00* (2011.01)

(52) U.S. Cl.
CPC .......... *A61B 5/0011* (2013.01); *A61B 5/0013* (2013.01); *A61B 5/0022* (2013.01);
(Continued)

(58) Field of Classification Search
CPC ... A61B 5/0011; A61B 5/0022; A61B 5/4343; A61B 5/435; A61B 5/4362; G06F 19/3418; G06F 19/345
See application file for complete search history.

(56) References Cited

U.S. PATENT DOCUMENTS

| 6,200,279 | B1  | 3/2001 | Paltieli |             |
|-----------|-----|--------|----------|-------------|
| 7,207,941 | B2* | 4/2007 | Sharf    | A61B 5/0031 |
|           |     |        |          | 600/438     |

(Continued)

OTHER PUBLICATIONS

International Search Report, mailing date Feb. 21, 2013 for corresponding International Application No. PCT/SG2012/000473.
(Continued)

*Primary Examiner* — Max Hindenburg
(74) *Attorney, Agent, or Firm* — Intellectual Property Law Group LLP

(57) ABSTRACT

There is provided a system of transmitting partograph information and analyzing the same comprising a client device adapted to receive partograph information as inputs; the inputs transmittable to a partograph processing server via a wireless communication network; wherein the partograph processing server is configured to receive the partograph information; conform the partograph information to a standardized format and disseminate the partograph information to at least one computer device. Preferably, the partograph processing server further comprises an analyzer to analyze the partograph information for one or more abnormality condition and provides an alert to the at least one computer device and the client device. Alternatively, the analyzer is installed in the client device in the form of a software application.

8 Claims, 4 Drawing Sheets

(52) U.S. Cl.
CPC ............ *A61B 5/435* (2013.01); *A61B 5/4362* (2013.01); *A61B 5/7282* (2013.01); *A61B 5/743* (2013.01); *A61B 5/746* (2013.01); *G06F 19/345* (2013.01); *G06F 19/3418* (2013.01); *A61B 5/742* (2013.01)

(56) References Cited

U.S. PATENT DOCUMENTS

| | | |
|---|---|---|
| 8,126,728 B2 * | 2/2012 | Dicks ................... A61B 5/0022 600/300 |
| 2004/0254430 A1 | 12/2004 | Hamilton |
| 2006/0282019 A1 | 12/2006 | Hamilton |
| 2008/0039744 A1 | 2/2008 | Hamilton |
| 2008/0097550 A1 | 4/2008 | Dicks et al. |
| 2008/0097908 A1 | 4/2008 | Dicks et al. |

OTHER PUBLICATIONS

International Preliminary Report on Patentability, mailing date Mar. 13, 2014 for corresponding International Application No. PCT/SG2012/000473.

\* cited by examiner

Fig. 2

| PARTOGRAPH | | | | | | | | | | | | | |
|---|---|---|---|---|---|---|---|---|---|---|---|---|---|
| USE THIS FORM FOR MONITORING ACTIVE LABOUR | | | | | | | | | | | | | |
| | 10 cm | | | | | | | | | | | | |
| | 9 cm | | | | | | | | | | | | |
| | 8 cm | | | | | | | | | | | | |
| | 7 cm | | | | | | | | | | | | |
| | 6 cm | | | | | | | | | | | | |
| | 5 cm | | | | | | | | | | | | |
| | 4 cm | | | | | | | | | | | | |
| FINDINGS | TIME | 1 | 2 | 3 | 4 | 5 | 6 | 7 | 8 | 9 | 10 | 11 | 12 |
| Hours in active labour | | | | | | | | | | | | | |
| Hours since ruptured membranes | | | | | | | | | | | | | |
| Rapid assessment | | | | | | | | | | | | | |
| Vaginal bleeding (0 + ++) | | | | | | | | | | | | | |
| Amniotic fluid (meconium stained) | | | | | | | | | | | | | |
| Contractions in 10 minutes | | | | | | | | | | | | | |
| Fetal heart rate (beats/minute) | | | | | | | | | | | | | |
| Urine voided | | | | | | | | | | | | | |
| T (axillary) | | | | | | | | | | | | | |
| Pulse (beats/minute) | | | | | | | | | | | | | |
| Blood pressure (systolic/diastolic) | | | | | | | | | | | | | |
| Cervical dilatation (cm) | | | | | | | | | | | | | |
| Delivery of placenta (time) | | | | | | | | | | | | | |
| Oxytocin (time/given) | | | | | | | | | | | | | |
| Problem-note onset/describe below | | | | | | | | | | | | | |

Fig. 4

SYSTEM AND METHOD FOR TRANSMITTING, RECEIVING AND ANALYSING PARTOGRAPH INFORMATION

CROSS-REFERENCE TO RELATED APPLICATIONS

This application is a U.S. National Phase application, under 35 U.S.C. §371, of International Application no. PCT/SG2012/000473, with an international filing date of Dec. 13, 2012, and claims benefit of Singapore Application no. 201109211-1 filed on Dec. 13, 2011, and which are hereby incorporated by reference for all purposes.

FIELD OF THE INVENTION

The present invention relates to a system and method for transmitting, receiving partograph information and analysing the same. The system and method are particularly suited for transmitting partograph information via a communications network and will be described in this context.

BACKGROUND ART

The following discussion of the background to the invention is intended to facilitate an understanding of the present invention only. It should be appreciated that the discussion is not an acknowledgement or admission that any of the material referred to was published, known or part of the common general knowledge of the person skilled in the art in any jurisdiction as at the priority date of the invention.

Partograms or partographs have been used to monitor the labour process of a pregnant woman and thereby aid in safe delivery. Traditionally, partographs are based on manual recording, which is inefficient and prone to mistakes arising from handwriting legibility and related issues which may result in misinterpretation and/or misreading of information, for example.

Electronic partographs alleviate the manual recording described above to certain extent. Electronic partographs such as the ePartogram (www.epartogram.eu) record labour data and develops a chart with an alert and action line, in accordance to the standard of management and criteria as formalized by the World Health Organisation Partogram.

While electronic partographs alleviate the disadvantages associated with manual recording to a certain extent, current electronic partographs do not have an effective way of collating, sharing and analysing the partograph information so as to enable, assist or notify the relevant medical practitioner(s) to reach a prompt and fast decision. In addition, current electronic partographs may be difficult to use or understand due to lack of a standardized method of presentation.

In addition to the above, there also exist a need for partograph information to be readily available in mobile devices to facilitate convenience and ease of use so as to help the relevant medical practitioner(s) to reach a prompt and fast decision.

The invention seeks to alleviate one or more of the above mentioned problems.

SUMMARY OF THE INVENTION

In accordance with a first aspect of the present invention, there is provided a system for transmitting, receiving and analysing partograph information comprising a client device adapted to receive partograph information as inputs; the partograph information transmittable to a partograph processing server via a communication network; wherein the partograph processing server is arranged to receive the partograph information; conform the partograph information to a standardized format and disseminate the partograph information to at least one computer device.

Preferably, the partograph processing server comprises an analyser to analyse the received partograph information for determination of at least one abnormality condition.

Preferably, the client device comprises an analyser to analyse the partograph information for determination of at least one abnormality condition.

Preferably, the partograph information includes cervical dilatation per unit time and fetal station per unit time.

The mentioned analyser preferably comprises a detection algorithm for detection of the at least one of the following abnormality conditions: Protracted active phase; Secondary arrest of cervical dilatation; prolonged deceleration phase; Failure of descent; protracted descent; and Arrest of descent.

Preferably, the communication network is a telecommunication network.

Preferably, the partograph information may be transmitted as Short Messaging Service (SMS) message(s), Unstructured Supplementary Service Data (USSD) messages, and/or via cellular data network such as GPRS, 3G, etc.

Preferably, an alert in the form of a notification message is generated when an abnormality condition is determined. The alert may be an SMS or USSD message.

In accordance with a second aspect of the present invention, there is provided a method for transmitting, receiving and analysing partograph information comprising the steps of: a. receiving from a client device, partograph information; b. transmitting the received partograph information to a partograph information processing server; c. processing the partograph information to conform a standardized format; and d. disseminating the processed information to at least one computer device.

Preferably, the method comprises a step of analysing the partograph information to determine if there is at least one abnormality condition prior to disseminating the processed information.

Preferably, the method further comprises the step of generating an alert to prompt the user of the client device and/or the computer device when an abnormality condition is determined.

Preferably, the partograph information includes cervical dilatation per unit time and fetal station per unit time.

Preferably, the abnormality condition include at least one of the following:—Protracted active phase; Secondary arrest of cervical dilatation; prolonged deceleration phase; Failure of descent; protracted descent; and Arrest of descent.

Preferably, the partograph information may be transmitted as Short Messaging Service (SMS) message(s), Unstructured Supplementary Service Data (USSD) messages, and/or via cellular data network such as GPRS, 3G, etc.

In accordance with a third aspect of the present invention there is a mobile device containing computer software instructions wherein upon execution of the software instructions perform any of the method according to the second aspect, wherein the mobile device is the client device.

BRIEF DESCRIPTION OF THE DRAWINGS

The present invention will now be described, by way of example only, with reference to the accompanying drawing, in which:

FIG. 2 illustrates a user interface of a system for transmitting partograph information and analysing the same in accordance to an embodiment of the invention, FIG. 4 illustrates an exemplary partograph provided by the World Health Organization (WHO) which may be used with the embodiments of the invention.

Figure 1:
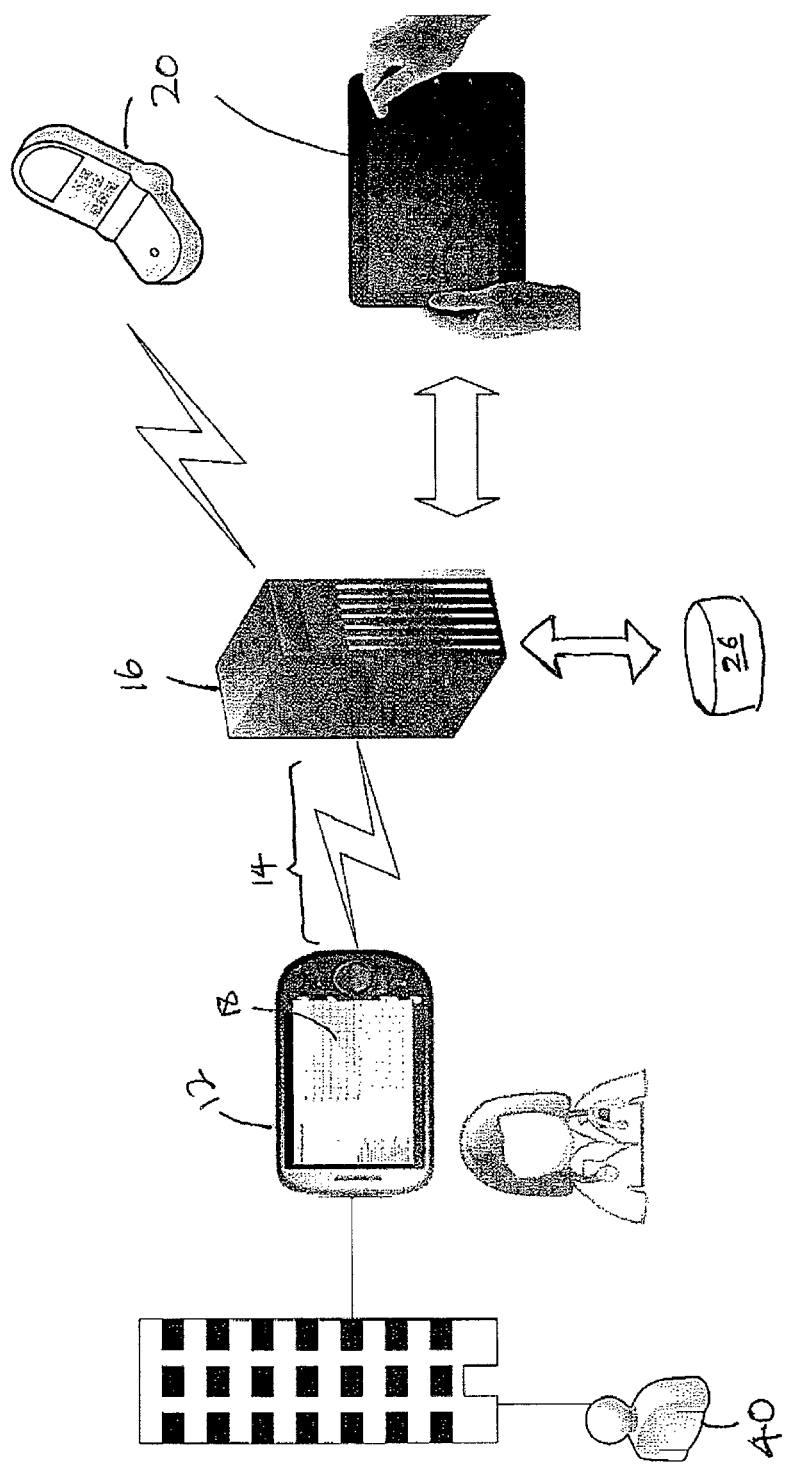
FIG. 1 is a schematic representation of a system for transmitting partograph information and analysing the same in accordance to an embodiment of the invention.

Other arrangements of the invention are possible and, consequently, the accompanying drawings are not to be understood as superseding the generality of the preceding description of the invention.

PREFERRED EMBODIMENTS OF THE INVENTION

In accordance with an embodiment of the present invention there is a system 10 for transmitting, receiving partograph information and analysing the same. In the context of the embodiment, the transmission and receipt of partograph information is between a client device 12 and a communication network 14.

The client device 12 is capable of data communication with the communication network 14. Preferably, communication network 14 is a wireless communication network. Where communication network 14 is a wireless communication network, the data communication may be via various communication protocols including but not limited to WiFi, GPRS, 3G, Enhanced Data rates for GSM Evolution (EDGE) etc.

Client device 12 may be a personal computer, a laptop computer, a mobile phone or any other computing device. As a minimum requirement, the client device 12 should be capable of transmitting and receiving partograph information in the form of simple text and capable of communicating via at least one communication protocol as described above.

As an illustrative example, client device 12 is preferably a smartphone. Smartphone 12 may be installed with a dedicated software application 18 specially suited for the transmission and receipt of partograph information. Dedicated software application 18 may be an application or 'app' as colloquially known, specifically for downloads for 'Android™', 'Iphone™' or other platforms for smartphones as known to a skilled person.

The dedicated software application 18 comprises a user-interface for a user of client device 12 to input partograph information and data including, but not limited to:
 a. Personal information such as name, age, admission date into a medical facility, time labour starts etc.
 b. Initial assessment information, which is to be input by a suitably qualified medical practitioner—including cervical dilation; fetal station (i.e. the relationship between the presenting part of the baby: the head, shoulder, buttocks, or feet and two parts of the mother's pelvis called the ischial spines); ruptured membranes (if any); time since ruptured of membranes; colour of amniotic fluid; whether there is an onset of true labour; contraction observed per minute; whether there is vaginal bleeding etc; and
 c. Monitored conditions as labour progresses—including Fetal Heart rate; blood pressure; pulse; urine output U/O and whether oxytocin (to facilitate birth) has been administered/started or stopped.

Figure 2:
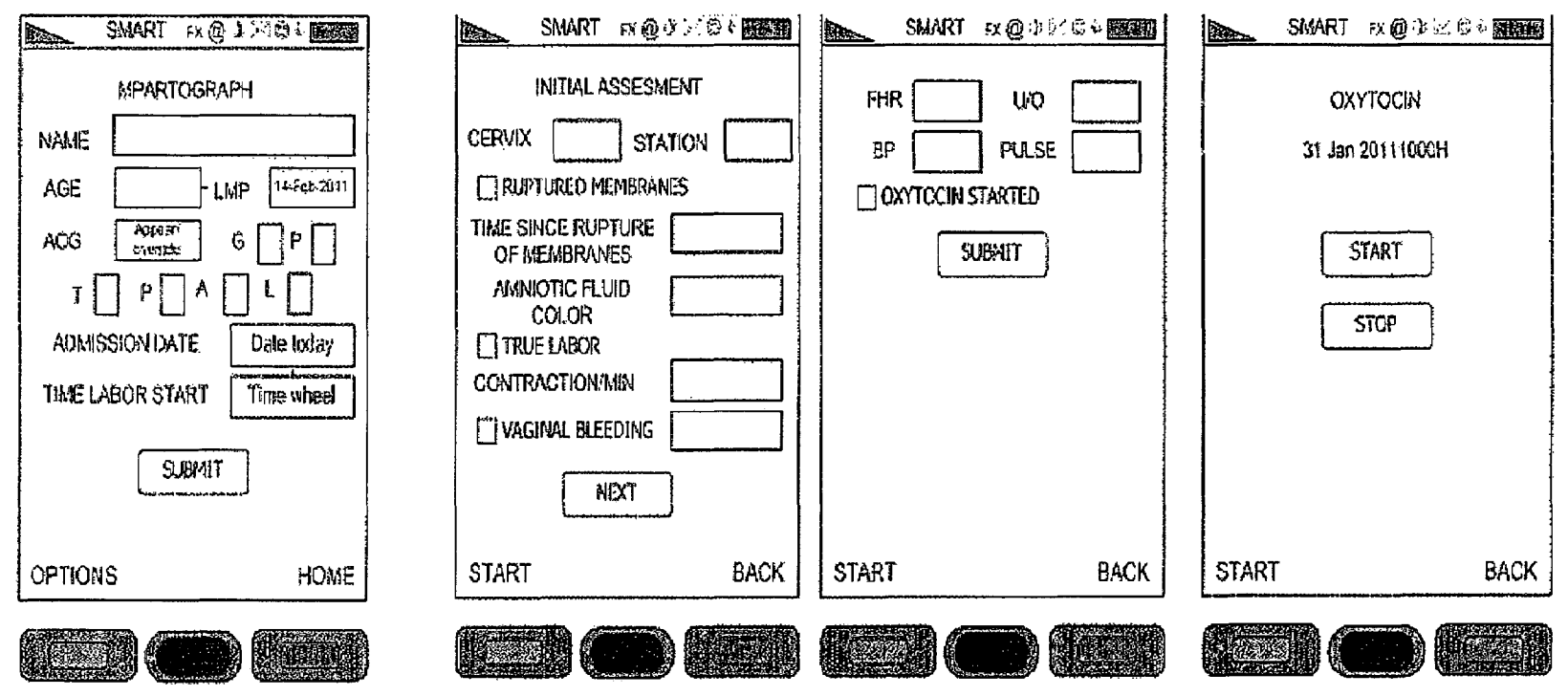

An illustrative example of the user-interface of the dedicated software app 18 is shown in FIG. 2.

The dedicated software application 18 may include an algorithm (described later) for analysing one or more of the partograph information as indicated in items a to c above.

Wireless communication network 14 may be part of, but is not limited to, a telecommunications network. Wireless communication network 14 is operable to be in data communication with a partograph processing server 16.

Partograph processing server 16 is adapted to receive inputs from the client device 12. As an alternative to the installation of analysis algorithm on client device 12, partograph processing server 16 may also be installed with software comprising the algorithm for analysing the partograph information received from client device 12 and returning an output indicative of the labour condition/progression of a patient 40.

Partograph processing server 16 may be configured to accept input from the client device 12 via different data connections. The mobile device 12 may use a telecommunications network, regular Internet connection over WiFi, SMS/MMS, etc to send the input data to the partograph processing server 16. The processing server 16 further includes a Secured Health information network and exchange (SHINE) system developed for providers of health care to share health data related to patients. Upon receiving the input data, partograph processing server 16 conform the received partograph information to a standardized format for dissemination. An example of such a format is the modified WHO partograph as illustrated in FIG. 4. The standardized format may be sent to at least one computer device 20 and/or back to the client device 12. Connection between the partograph processing server 16 and the at least one computer device 20 may be either via physical data connection or wireless means.

Partograph processing server 16 may further include a database 26, the database 26 for storing the profile of each user, whom may be patients. Suitable security settings on the database 26 are necessary to maintain privacy of each user.

Figure 3:
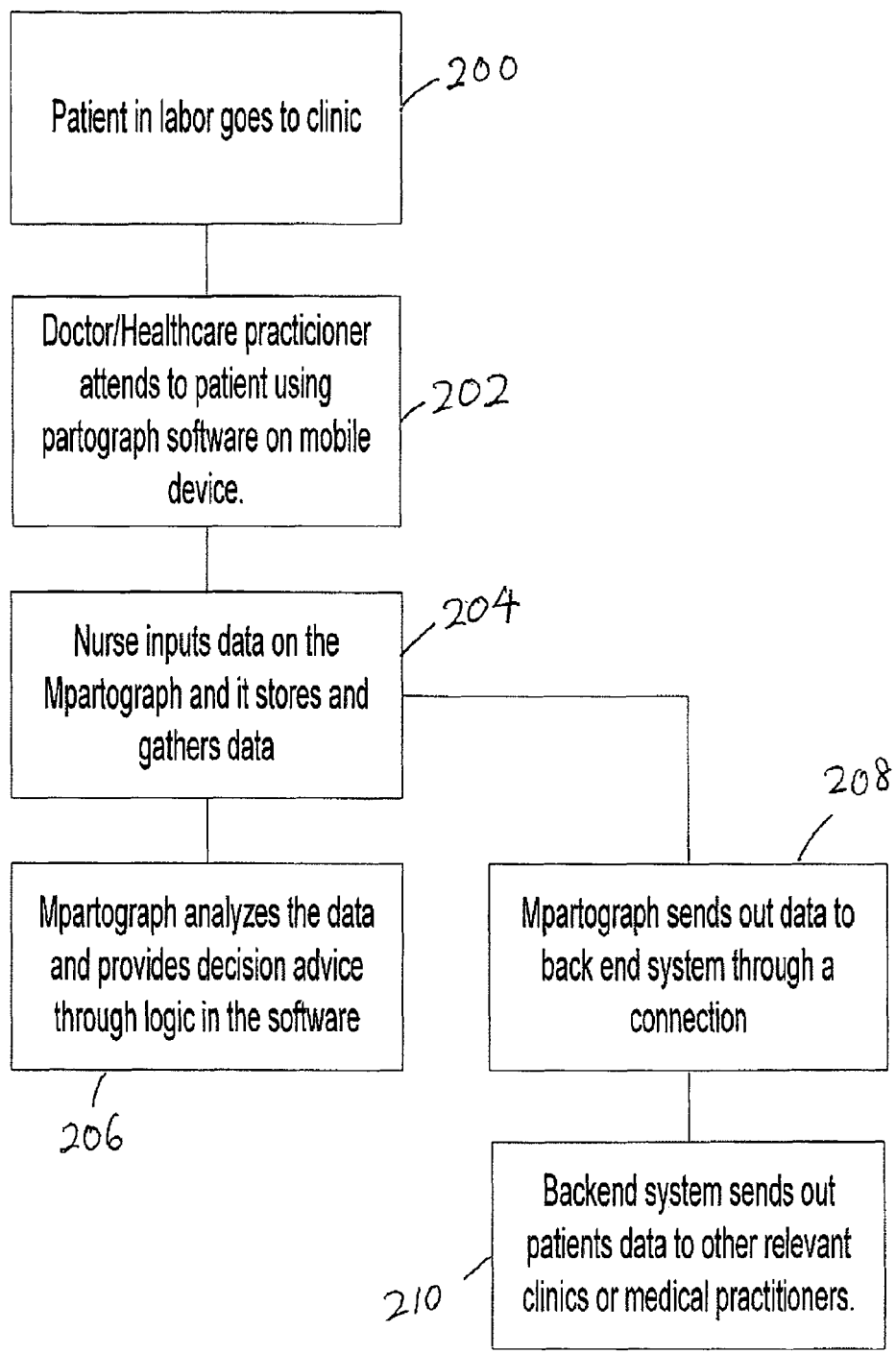
FIG. 3 is a flow chart of a method for transmitting partograph information and analysing the same.

The operation of the system 10 in the context of a user of client device 12 sending partograph information to the partograph processing server 16 is described with reference to FIG. 3 as follows. The user of client device 12 is generally a medical practitioner or medical worker.

At step 200, a patient 40 in labour goes to the medical facility (maternity clinic for example). A medical practitioner, such as a doctor or other qualified medical personnel attends to the patient—step 202. An assistant (who is a medical worker), usually a nurse may help to record the data in the partograph using the client device 12 installed with the dedicated partograph software app (also known as 'Mpartograph')—step 204.

The Mpartograph analyses the data inputted and provides decision advice based on the algorithm installed in the software—step 206. Where the client device is not installed with the Mpartograph software, the analysis may alternatively be performed at the partograph processing server 16 which is also installed with Mpartograph.

The analysed information is sent to the partograph processing server 16 via the telecommunications network 14—step 208. The partograph processing server 16 also send the partograph data to other computing devices 20. Computing devices 20 may be the working desktops of other related medical practitioners such as midwives, anaesthetist etc.

The decision logic and analysis of the partograph information is performed as follows:

The step of analysing the partograph information is based on an algorithm.

The algorithm is based on detection of the following abnormalities based on the inputs received:
a. Protracted active phase;
b. Secondary arrest of cervical dilatation;
c. Prolonged deceleration phase;
d. Failure of descent;
e. Protracted descent; and
f. Arrest of descent The pseudocode and algorithm for analysing the partograph information for the purpose of determining each abnormality is described as follows:

a. Protracted Active Phase
Pseudo-code (based on cervical dilation as a function of time)
  i. If cervical dilatation ≥4 cm and parity=0 and trendline after 4 cm shows <1.2 cm dilation/hour OR
  ii. If cervical dilatation ≥4 cm and parity ≥1 and trendline after 4 cm shows <1.5 cm dilation/hour then show alert
Alert message may be in the form of: "Patient may be in Protracted active phase. Check for fetal malposition, CPD, or hypotonic contractions. Refer if needed"

b. Secondary Arrest of Cervical Dilatation
Pseudo-code (based on cervical dilation as a function of time)
  i. If cervical dilatation ≥4 cm and no increase in dilatation after two hours then show alert
Alert message may be in the form of: "Patient may be in Secondary arrest of cervical dilatation. Check for CPD, fetal malposition, or hypotonic uterine contractions"

c. Prolonged Deceleration Phase
Pseudo-code (based on cervical dilation as a function of time)
  i. if cervical dilatation is >9 cm and cervical dilatation <10 cm and parity=0 and time elapsed for cervical dilation to reach 10 is >1 hour then show alert OR
  ii. if cervical dilatation is >9 and cervical dilatation <10 and parity ≥1 and time elapsed for cervical dilation to reach 10 is >1 hour then show alert
Alert message may be in the form of: "Patient may be in prolonged deceleration phase. If fetal station greater than or=to +1 then check for fetal malposition or hypotonic contraction, if fetal station is less than +1 then consider CPD"

d. Failure of Descent
Pseudo-code (based on cervical dilation as a function of time and fetal station as a function of time)
  i. If cervical dilatation=10 and fetal station=−4 and more than 1 hour has elapsed and no change in fetal station then show alert
Alert message may be in the form of: "There is Failure of descent due to CPD. Refer immediately."

e. Protracted Descent
Pseudo-code (based on cervical dilation as a function of time and fetal station as a function of time)
  i. If parity=0 and cervical dilation=10 cm and fetal station is >−4 and trendline shows <1 station change/hour OR
  ii. If parity ≥4 and cervical dilation=10 cm and fetal station is >−4 and trendline shows <2 station change/hour
Alert message may be in the form of: "Patient may be in Protracted Descent. consider CPD, hypotonic contraction, fetal malposition"

f. Arrest of Descent
Pseudo-code (based on cervical dilation as a function of time and fetal station as a function of time)
  i. If cervical dilatation=10 cm and parity=0 and fetal station is >−4 and no change in fetal station after more than 2 hours
Alert message may be in the form of: "Patient may be in Arrest of Descent consider hypotonic contraction, fetal malposition, CPD. Refer if needed"

In accordance with another embodiment of the present invention there is a method 100 for transmitting partograph information and analysing the same. The method comprises the steps of:—receiving at a client device 12 partograph information; transmitting the partograph information to the partograph processing server 16; conforming the partograph information to a standardized format; disseminating the partograph information to at least one computer device 20 and analysing the partograph information to determine at least one or more condition and optionally returning an alert to the computer device 20. The partograph information refers to the following parameters as inputs:—a. one is the cervical dilatation as a function of time; and b. fetal station as a function of time.

Other possible partograph information may be found at the following website: www.who.int, in a "Making Pregnancy Safer" document particularly on page 170 which refers to the following parameters/inputs of the modified WHO partograph (page 170), including, but not limited to:
1. Hours since ruptured membranes
2. Rapid assessment
3. Vaginal bleeding
4. Amniotic fluid
5. Number of contraction(s) in 10 min.
6. Fetal heart rate
7. Urine voided
8. Temp
9. Pulse
10. BP
11. Delivery of placenta
12. Oxytocin
13. Problem-note (this would be other findings)

In particular, the Rapid assessment under item 2 further comprises a drop down list with the following conditions:
  i. Difficulty Breathing
  ii. Cyanosis
  iii. Cold and moist skin
  iv. Weak and fast pulse
  v. Convulsing
  vi. Unconsciousness
  vii. Severe abdominal pain
  viii. Fever >38 C and very fast breathing/stiff neck/lethargy/weak It is to be appreciated that any chosen condition related to rapid assessment will trigger a prompt/alert on at least the client device 12 to the effect that urgent referral is required, for example:

"Patient needs to be stabilized in a CEMONC center. Refer as needed"

The step of analysing the partograph information is based on the algorithm as earlier described in the previous embodiment.

The present invention addresses the limitation of prior art by providing a decision making tool logic based on the responses made on the fields of the partograph.

The traditional setup of existing electronic or manual partograph would be to fill up the form and then sending out copies of it (through mail, fax, scanned copies or through the patient themselves) to the medical practitioner/doctor who needs it. The disadvantage with this setup is that it is very open to the data being misplaced, or even being lost in translation. The partograph, while having a standardized format and fields, may have different interpretations according to the person who reads them.

The proposed invention seeks to circumvent this issue by providing a standardized method of sending the partograph information to a backend processing server (i.e. the partograph processing server 16), and the recipient being able to read this data in a standardized format that would be easy to understand.

It is to be understood that the above embodiments have been provided only by way of exemplification of this invention, such as those detailed below, and that further modifications and improvements thereto, as would be apparent to persons skilled in the relevant art, are deemed to fall within the broad scope and ambit of the present invention described:

- Health providers in the described embodiment may mean any facility that provides medical services to patients. These could range from clinics, wards, infirmaries, and hospitals.
- The client device may preferably be a smart phone but could actually be any kind of mobile device that is equipped with the capability to connect to an existing mobile network and utilize its services such as voice calling and SMS.
- The invention, i.e. the mobile partograph would be sending out data in real time to a medical practitioner who may not be in the premises where the patient is in labor. For such a setup to work, the invention should now be coupled with a mechanism that would enable real time data processing and communication.
- Where the mobile device is a laptop or desktop computer, the dedicated software application 18 may be in the form of a web based application providing a user-interface for login and entry of partograph data.
- The algorithm for analyzing the partograph information may be installed on the client device 14 or present in the partograph processing server 16.

It is to be further appreciated that various aspects of the embodiments as described may be combined to form further embodiments without departing from the scope of the invention.

The invention claimed is:

1. A system for transmitting, receiving and analysing partograph information comprising:
   a mobile device adapted to receive partograph information as inputs; the partograph information transmittable to a partograph processing server via a communication network;
   wherein the partograph processing server is arranged to: access a database to receive profile information of a patient, conform the partograph information to a standardized partograph format, and disseminate the partograph information to at least one computer device, and
   wherein the partograph processing server comprises an analyser configured to analyse and use, from the partograph information transmittable to the partograph processing server, cervical dilation per unit time information and/or fetal station per unit time information as input for detection of at least one abnormality condition.

2. A system according to claim 1, wherein the database comprises security settings to maintain privacy of the patient.

3. A system according to claim 1, wherein the analyser comprises a detection algorithm configured to use cervical dilatation per unit time or fetal station per unit time as inputs for detection of at least one of the following abnormality conditions: Protracted active phase; Secondary arrest of cervical dilatation; prolonged deceleration phase; Failure of descent; protracted descent; and Arrest of descent.

4. A system according to claim 1, wherein the communication network is a telecommunication network.

5. A system according to claim 4, wherein the partograph information may be transmitted as Short Messaging Service (SMS) message(s), Unstructured Supplementary Service Data (USSD) messages, and/or via cellular data network such as GPRS, and 3G.

6. A system according to claim 1, wherein an alert in the form of a notification message is generated when the at least one abnormality condition is determined.

7. A system according to claim 6, wherein the alert is a SMS or USSD message.

8. A system for transmitting, receiving and analysing partograph information comprising:
   a mobile device adapted to receive partograph information as inputs; the partograph information transmittable to a partograph processing server via a communication network;
   wherein the partograph processing server is arranged to: receive profile information of a patient, conform the partograph information to a standardized partograph format, and disseminate the partograph information to at least one computer device, and
   wherein the partograph processing server comprises an analyser configured to analyse and use, from the partograph information transmittable to the partograph processing server, cervical dilation per unit time information and/or fetal station per unit time information as input for detection of at least one abnormality condition.

* * * * *